US012599702B2

(12) United States Patent
Suzuki et al.

(10) Patent No.: US 12,599,702 B2
(45) Date of Patent: Apr. 14, 2026

(54) BONE REGENERATION MATERIAL

(71) Applicant: NIPRO CORPORATION, Osaka (JP)

(72) Inventors: Osamu Suzuki, Sendai (JP);
Yoshikatsu Sugahara, Osaka (JP);
Satoshi Urai, Osaka (JP); Yusuke Nakamura, Osaka (JP)

(73) Assignee: NIPRO CORPORATION, Osaka (JP)

( * ) Notice: Subject to any disclaimer, the term of this patent is extended or adjusted under 35 U.S.C. 154(b) by 938 days.

(21) Appl. No.: 17/274,893

(22) PCT Filed: Oct. 3, 2019

(86) PCT No.: PCT/JP2019/039172
§ 371 (c)(1),
(2) Date: Mar. 10, 2021

(87) PCT Pub. No.: WO2020/071497
PCT Pub. Date: Apr. 9, 2020

(65) Prior Publication Data
US 2022/0054712 A1 Feb. 24, 2022

(30) Foreign Application Priority Data
Oct. 4, 2018 (JP) ................................ 2018-189243

(51) Int. Cl.
*A61L 27/46* (2006.01)
*A61L 27/56* (2006.01)
(52) U.S. Cl.
CPC .............. *A61L 27/46* (2013.01); *A61L 27/56* (2013.01); *A61L 2400/12* (2013.01); *A61L 2430/02* (2013.01)
(58) Field of Classification Search
CPC .. A61L 27/46; A61L 2430/02; A61L 2400/12; A61L 27/56; A61L 27/12; A61L 27/22; A61L 27/40
See application file for complete search history.

(56) References Cited

U.S. PATENT DOCUMENTS 10,064,979 B2 * 9/2018 Suzuki .................... A61L 27/46
2011/0014266 A1 1/2011 Shoji 2014/0050789 A1 * 2/2014 Rogawski .......... A61K 31/5517
514/289
2017/0049933 A1 * 2/2017 Suzuki .................. A61L 27/222
2017/0246343 A1 * 8/2017 Zhang ..................... A61L 27/58

FOREIGN PATENT DOCUMENTS

| | | |
|---|---|---|
| JP | 5458237 B2 | 4/2014 |
| JP | 5647432 B2 | 12/2014 |
| JP | 5881206 B2 | 3/2016 |

OTHER PUBLICATIONS

Handa et al., "The effect of an octacalcium phosphate co-precipitated gelatin composite on the repair of critical-sized defects" in Acta Biomaterialia, 8 (2012) 1190-1200 (Year: 2012).*
31. Muira et al., "Characterization and bioactivity of nano-submicron octacalcium phosphate/gelation composite," in Applied Surface Science, 282 (2013) 138-145. (Year: 2013).*
32. Suzuki, "Octacalcium phosphate (OCP)-based bone substitute materials," in SciVerse Science Direct, available online Apr. 15, 2013, pp. 58-71. (Year: 2013).*
Risa Ishiko-Uzuka, "Oriented bone regenerative capacity of octacalcium phosphate/gelatin composites obtained through a two-step crystal preparation method" in J Biomed Mater Res Part B 2017:105B:1029-1039 (Year: 2017).*
Handa, T. et al., "The effect of an octacalcium phosphate co-precipitated gelatin composite on the repair of critical-sized rat calvarial defects," Acta Biomaterialia, vol. 8, No. 3, Dec. 13, 2011, 11 pages.
Panzavolta, S. et al., "Porous composite scaffolds based on gelatin and partially hydrolyzed a-tricalcium phosphate," Acta Biomaterialia, vol. 5, No. 2, Sep. 10, 2008, 8 pages.

* cited by examiner

*Primary Examiner* — Blessing M Fubara
(74) *Attorney, Agent, or Firm* — Alleman Hall LLP

(57) ABSTRACT

A bone regeneration material according to the present disclosure includes at least a composite of octacalcium phosphate (OCP) particles and gelatin, and is a porous body having a plurality of pores. The particle size of the octacalcium phosphate particles is 1 μm or more but less than 1 mm, and the molecular weight of the gelatin is in the range of 30 kDa to 70 kDa. Thus, the material is able to resist breaking down during implantation and exhibit high handleability.

10 Claims, 2 Drawing Sheets

Number of test cycles

BONE REGENERATION MATERIAL

TECHNICAL FIELD

The present invention relates to a bone regeneration material in the form of a composite of a calcium phosphate compound and a polymer material and particularly relates to a bone regeneration material prepared using gelatin as the polymer material.

BACKGROUND ART

Bone regeneration materials are used, for example, as substitutes for lost bones or as fillings for defect sites of bones. Various substances are known as components of the bone regeneration materials, and a typical example of the bone regeneration materials is one prepared using a calcium phosphate compound. Examples of the calcium phosphate compound include hydroxyapatite (HAp or HAP), β-tricalcium phosphate (β-TCP), and octacalcium phosphate (OCP).

These calcium phosphate compounds generally have high brittleness and low formability. When using such a calcium phosphate compound in a bone regeneration material, it is common practice to sinter the calcium phosphate compound into the shape of a block or form a composite using a polymer material together with the calcium phosphate compound. A typical example of the polymer material used together with the calcium phosphate compound is collagen.

Such a bone regeneration material as prepared using collagen will be referred to as a "collagen-containing bone regeneration material" for convenience of explanation. A typical example of the collagen-containing bone regeneration material is an expandable porous body disclosed in Patent Literature 1. This expandable porous body is a compressed composite of apatite and collagen. The porous body is adapted to maintain the shape as formed by compression when in a dry state and expand into the pre-compression state upon absorbing water. Some of such collagen-containing bone regeneration materials have already received medical device manufacturing and marketing approval and are covered by insurance (an example is one sold under the name "ReFit" (registered trademark)).

Other bone regeneration materials are proposed by the present applicants in Patent Literatures 2 and 3. These bone regeneration materials differ from the above collagen-containing bone regeneration material by being prepared using gelatin as the polymer material. Such a bone regeneration material as prepared using a calcium phosphate compound and gelatin will be referred to as a "gelatin-containing bone regeneration material" to distinguish it from the above collagen-containing bone regeneration material.

The bone regeneration material (gelatin-containing bone regeneration material) disclosed in Patent Literature 2 includes a thermally-dehydrated cross-linked coprecipitate of octacalcium phosphate and gelatin. The bone regeneration material (gelatin-containing bone regeneration material) disclosed in Patent Literature 3 includes a composite of a fine octacalcium phosphate powder having a particle size of 5 to 1000 nm and gelatin, and has air voids (pores) with a size of 10 to 500 μm. These bone regeneration materials can exhibit high physical strength or good physical properties such as suitable formability and elastic modulus. Additionally, they can exhibit such high bone regeneration performance that they can well replace new bones.

CITATION LIST

Patent Literature

PTL 1: Japanese Patent No. 5458237
PTL 2: Japanese Patent No. 5647432
PTL 3: Japanese Patent No. 5881206

SUMMARY OF INVENTION

Technical Problem

The collagen-containing bone regeneration material disclosed in Patent Literature 1 has elasticity when wetted. Thus, this material is alleged to exhibit high conformability when implanted into a bone defect site and to be easily workable by a tool such as a scalpel or scissors. In fact, however, the collagen-containing bone regeneration material has been found so fragile that it tends to be broken down when held with a tool such as tweezers. For example, the collagen-containing bone regeneration material is likely to be broken down into tiny pieces (fines or "debris") during implantation into a bone defect site.

The bone regeneration materials (gelatin-containing bone regeneration materials) disclosed in Patent Literatures 2 and 3, in which gelatin is used instead of collagen, can exhibit good physical properties and high bone regeneration performance as stated in the literatures. However, it has been found also for these gelatin-containing bone regeneration materials that there is room for improvement in terms of handleability.

The present invention has been made to solve the problems described above, and an object of the present invention is to provide a gelatin-containing bone regeneration material able to resist breaking down during implantation and exhibit high handleability.

Solution to Problem

In order to solve the problems described above, a bone regeneration material according to the present invention includes at least a composite of octacalcium phosphate particles and gelatin, the bone regeneration material being a porous body having a plurality of pores, wherein a particle size of the octacalcium phosphate particles is 1 μm or more but less than 1 mm, and a molecular weight of the gelatin is in a range of 30 kDa to 70 kDa.

The bone regeneration material as defined above is a bone regeneration material including a composite of a calcium phosphate compound and a polymer material as a main component, and the composite is an OCP-gelatin composite (OCP/Gel) formed by using micrometer-sized octacalcium phosphate particles (OCP particles) as the calcium phosphate compound and using gelatin having a molecular weight in a predetermined range as the polymer material. Thus, when soaked with water and then compressed, the bone regeneration material can remain free of damage such as fracture or breaking down and return substantially to the pre-compression original shape. That is, the bone regeneration material is superior in shape retaining property to conventional bone regeneration materials, and can be obtained as a gelatin-containing bone regeneration material able to resist breaking down during implantation and exhibit high handleability.

In the bone regeneration material as defined above, a porosity may be in a range of 87% to 98%, the porosity being a volume ratio of the pores present in the porous body, and a median size of the pores may be in a range of 14 μm to 55 μm.

In the bone regeneration material as defined above, the particle size of the octacalcium phosphate particles may be in a range of 1 μm to 200 μm.

In the bone regeneration material as defined above, a mass ratio of the octacalcium phosphate particles to the gelatin in the composite may be in a range of 1 to 9.

The above and further objects, features and advantages of the present invention will be more apparent from the following detailed description of preferred embodiments with reference to the accompanying drawings.

Advantageous Effects of Invention

The present invention as defined above offers the advantage of providing a gelatin-containing bone regeneration material able to resist breaking down during implantation and exhibit high handleability.

DESCRIPTION OF EMBODIMENTS

Figure 1:
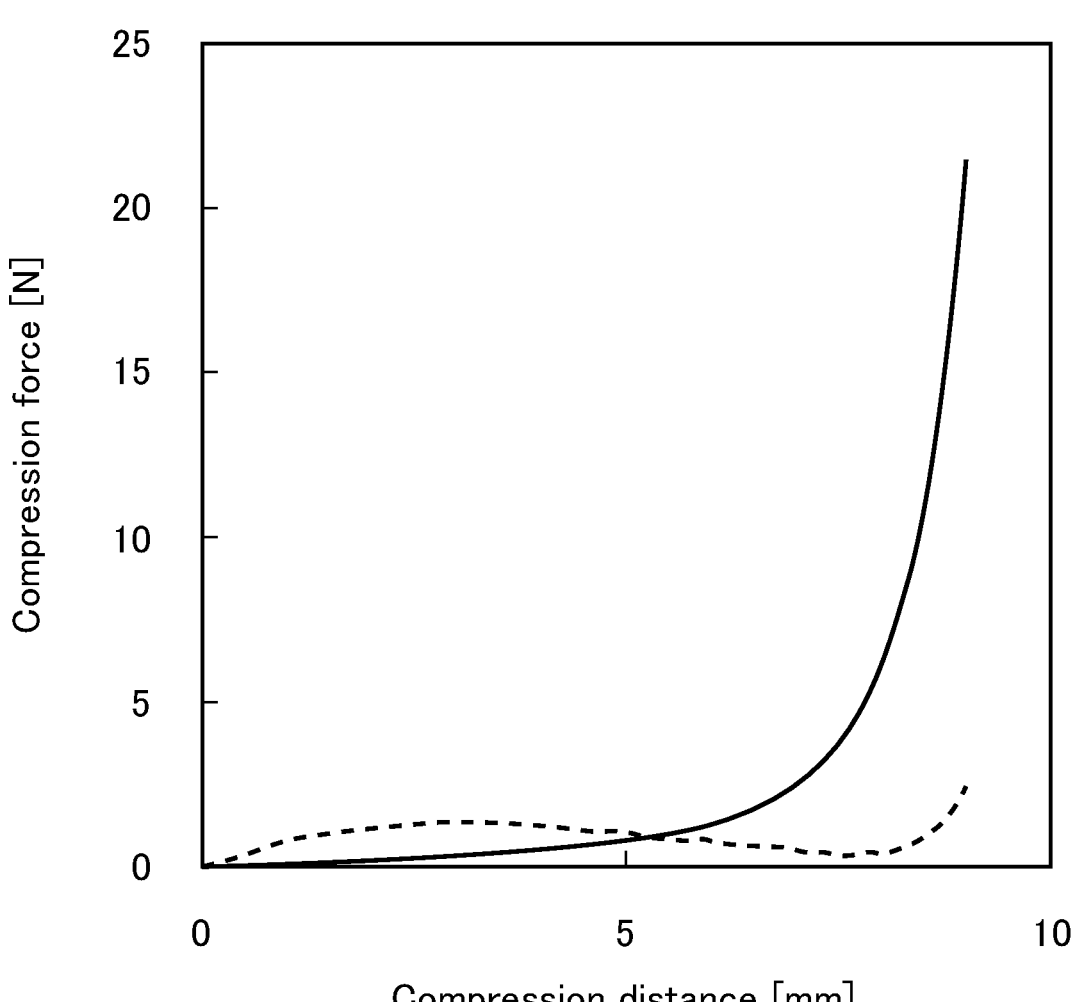
FIG. 1 is a graph showing the change in compression force with respect to compression distance in compression testing of bone regeneration material samples according to Example 1 of the present invention and Comparative Example 1.

A bone regeneration material according to the present disclosure includes at least a composite of octacalcium phosphate particles (OCP particles) and gelatin, and is a porous body having a plurality of air voids (pores). The particle size of the octacalcium phosphate particles of the composite is 1 μm or more but less than 1 mm. The molecular weight of the gelatin of the composite is in the range of 30 kDa to 70 kDa. Hereinafter, an exemplary embodiment of the present disclosure will be described in detail. In the following description, a composite of OCP particles and gelatin will occasionally be referred to as "OCP/Gel".

The OCP particles used in the present disclosure may be any OCP particles whose particle size is such that the median diameter (D50) is 1 μm or more but less than 1 mm, namely in the order of micrometers. Preferably, the particle size may be 1 μm or more and 100 μm or less. More preferably, the particle size may be in the range of 20 μm to 60 μm. If the particle size of the OCP particles is outside the above range, a bone regeneration material having the OCP particles dispersed well in the gelatin cannot be obtained. That is, in the present disclosure, a desired OCP/Gel cannot be obtained when the OCP particles are too large or small.

The method for measuring the particle size of the OCP particles is not limited to any particular method. A typical example of the method is one using a laser diffraction particle size distribution analyzer. In the present embodiment, for example, the particle size of the OCP particles is measured by a wet method using an analyzer manufactured by MicrotracBEL Corporation under the product name "Microtrac MT-3300 EX II".

The OCP particles according to the present disclosure may be any OCP particles having a particle size in the order of micrometers, and are not limited as to the other physical properties or preparation method. When OCP particles having a particle size in the order of micrometers are commercially available, such a commercially-available product can be used. When the OCP particles are prepared, for example, the preparation may be performed according to the method described in Patent Literature 3, and the conditions used may be chosen or adjusted to allow the particle size to fall within the predetermined range.

The gelatin used in the present disclosure has a molecular weight (or a molecular weight distribution) in the range of 30 kDa to 70 kDa. The term "molecular weight" as used herein refers to a weight-average molecular weight. The gelatin in the present disclosure may be a commercially-available product or may be prepared by denaturation of collagen. The method for collagen denaturation is not limited to any particular method, and a typical example of the method is to thermally treat collagen under known conditions.

When the gelatin in the present disclosure is prepared from collagen, the origin of the collagen used as the raw material is not limited to any particular origin. Examples of the collagen to be used include those derived from skin, bone, and tendon of swine and bovine. A preferred example of the collagen to be used is enzyme-solubilized collagen which has been solubilized by a known proteolytic enzyme and from which telopeptide has been removed. The type of the collagen to be used is not limited to any particular type, and typical examples of the collagen to be used include type I collagen, type II collagen, and type III collagen.

As previously stated, the molecular weight (or molecular weight distribution) of the gelatin used in the present disclosure is in the range of 30 kDa to 70 kDa. Preferably, the molecular weight may be in the range of 35 kDa to 65 kDa. More preferably, the molecular weight may be in the range of 40 kDa to 60 kDa.

If the molecular weight (or the lower limit of the molecular weight distribution) of the gelatin is less than 30 kDa, an OCP/Gel having the OCP particles dispersed well in the gelatin cannot be obtained. If the molecular weight (or the upper limit of the molecular weight distribution) of the gelatin is more than 70 kDa, an OCP/Gel having the OCP particles dispersed well in the gelatin (namely, a bone regeneration material or its main component) can be obtained indeed, but the shape retaining property of the OCP/Gel is so poor that the OCP/Gel cannot return to the original shape after compression or is fractured or broken down due to the compression.

The method for measuring the molecular weight of the gelatin is not limited to any particular method. In the present embodiment, for example, a method is used which is described in "20-2. Average Molecular Weight" of "PAGI method: methods for testing photographic gelatin, 10th edition, 2006" (issued by Commission on Methods for Testing Photographic Gelatin in November 2006).

The term "shape retaining property" in the present disclosure refers at least to the ability of the bone regeneration material to remain substantially free of "damage" when the material is soaked (wetted) with water and then compressed (pressed by an external force). The "damage" means a failure such as fracture or breaking down (fracture etc.) which precludes the bone regeneration material from maintaining the pre-compression original shape. The term "shape retaining property" in the present disclosure preferably refers to having not only the ability to remain substantially free of "damage" such as fracture etc. but also the ability (resilience) to return substantially to the original shape upon release from compression. The bone regeneration material according to the present disclosure has such shape retaining property and can therefore exhibit high handleability during implantation.

As previously stated, the bone regeneration material according to the present disclosure includes at least a composite (OCP/Gel) of OCP particles and gelatin. The proportion between the OCP particles and the gelatin (the ratio between their contents in the composite or between their amounts used in mixing) is not limited to any particular value. Typically, the mass ratio of the OCP particles to the gelatin may be in the range of 1 to 9. In other words, the ratio between the mass of the gelatin and the mass of the OCP particles (Gel:OCP) in the OCP/Gel may be from 1:1 to 1:9.

If the mass ratio of the OCP particles to the gelatin is less than 1, the bone regeneration performance of the resulting bone regeneration material tends to deteriorate, although this depends on various other factors. If the mass ratio of the OCP particles to the gelatin is more than 9, the formability of the resulting bone regeneration material is reduced.

Although it has been stated that the bone regeneration material according to the present disclosure includes at least a composite (OCP/Gel) of OCP particles and gelatin, the bone regeneration material may contain a component other than the OCP particles and the gelatin. Such a component may be a substance known in the field of bone regeneration materials, and examples of the substance include: bioabsorbable polymers other than gelatin, such as polylactic acid and polylactic acid-polyethylene glycol copolymer; calcium phosphate compounds other than OCP, such as β-tricalcium phosphate (β-TCP); non-bioabsorbable material, such as hydroxyapatite ceramics; etc. When the other component is contained in the bone regeneration material according to the present disclosure, the content of the other component is not limited to any particular value and may be any value as long as the other component does not adversely affect the physical properties or advantages of the bone regeneration material.

The method for producing the bone regeneration material according to the present disclosure is not limited to any particular method. For example, freeze-drying as disclosed in Patent Literature 3, rather than coprecipitation as disclosed in Patent Literature 2, may be used. The freeze-drying is not limited as to the details of the conditions to be employed, and may be performed using the conditions disclosed in Patent Literature 3 or in any other known document. The conditions disclosed in the known documents may be adjusted or changed as appropriate.

As previously stated, the bone regeneration material according to the present disclosure includes at least an OCP/Gel, and has a plurality of pores (or air voids). That is, the bone regeneration material according to the present disclosure is a porous body in the form of a composite of OCP particles and gelatin or a porous body including a composite of OCP particles and gelatin as a main component.

The pores of the bone regeneration material according to the present disclosure are not limited as to the details of their characteristics. The size of the pores (pore size or void size) may be such that the median size is in the range of 14 μm to 55 μm. Preferably, the median size of the pores may be in the range of 20 μm to 45 μm. More preferably, the median size may be in the range of 25 μm to 40 μm.

If the pore size is less than 14 μm, the entry of cells into the pores tends to be inhibited after implantation of the bone regeneration material, although this depends on various other factors. If the pore size is more than 55 μm, the strength or shape retaining property of the bone regeneration material tends to be reduced, although this depends on various other factors. The method for measuring the pore size is not limited to any particular method. A typical example of the method is one as described in Examples below which uses a pore size distribution analyzer.

Among the large number of pores present in the bone regeneration material according to the present disclosure, those having a pore size of more than 100 μm will be referred to as "large-size pores" for convenience of explanation. The ratio of the volume of the large-size pores to the total volume of all the pores (it should be noted that the pores are those having a pore size in the range of 0.01 μm to 500 μm) is not limited to any particular value. Typically, the volume ratio of the large-size pores may be 35% or less. Preferably, the upper limit of the volume ratio of the large-size pores may be 20% or less. More preferably, the upper limit may be 5% or less. The shape retaining property of the bone regeneration material could be reduced if the volume ratio of the large-size pores is more than 35%, although this depends on various other factors.

The method for calculating the volume ratio of the large-size pores is not limited to any particular method. An example of the method is to calculate the volume of the large-size pores and the total volume of all the pores through mercury intrusion using a pore size distribution analyzer and conditions as described in Examples below and divide the calculated volume of the large-size pores by the calculated total volume of all the pores.

The porosity of the bone regeneration material according to the present disclosure, i.e., the volume ratio of the pores present in the bone regeneration material which is in the form of a porous body, may be in the range of 88% to 98%. Preferably, the porosity may be in the range of 90% to 96%. If the porosity is less than 88%, the shape retaining property of the bone regeneration material tends to be reduced, although this depends on various other factors. A porous body with a porosity of more than 98% is generally difficult to produce, although this depends on various other factors.

The method for measuring the pore size and porosity is not limited to any particular method, and a typical example of the method is the above-mentioned mercury intrusion using a pore size distribution analyzer and conditions as described in Examples. The method for controlling the pore size and porosity of the bone regeneration material is not limited to any particular method. An example of the method is to adjust or vary the pore formation-related factors in the above-mentioned freeze-drying.

The bone regeneration material according to the present disclosure is not limited as to the details of its physical properties. For example, the elastic modulus of the bone regeneration material according to the present disclosure is not limited to any particular value, and may be in the range of $0.01 \text{ N/mm}^2$ to $0.1 \text{ N/mm}^2$. Preferably, the elastic modulus may be in the range of $0.015 \text{ N/mm}^2$ to $0.0750 \text{ N/mm}^2$. If the elastic modulus is less than $0.01 \text{ N/mm}^2$, the degree of resilience of the bone regeneration material could be so low as to be insufficient for practical use, although this depends on various other factors. If the elastic modulus is more than $0.1 \text{ N/mm}^2$, the bone regeneration material could be fractured or broken down upon repeated compression, although this depends on various other factors.

The method for measuring the elastic modulus is not limited to any particular method. A typical example of the method is one as described in Examples below which uses a compression tester. The bone regeneration material is wetted with water beforehand for the measurement of the elastic modulus.

The bone regeneration material according to the present disclosure exhibits a high degree of resilience when compressed. The bone regeneration material is not limited as to the details of the degree of resilience. Typically, when the bone regeneration material yet to be compressed is placed on a horizontal surface (reference surface) and the height of the bone regeneration material from the reference surface is defined as 100%, the height of the bone regeneration material as measured after compression is in the range of 90% to 100%. Preferably, the degree of resilience against compression may be in the range of 94% to 100%. If the degree of resilience against compression is 97% or more, the material can be rated as having excellent resilience.

When evaluated for the degree of resilience, the bone regeneration material is wetted with water and then compressed. To evaluate the degree of resilience, the bone regeneration material needs to be free of damage such as fracture or breaking down after compression. That is, if a bone regeneration material compressed suffers from damage such as fracture, the bone regeneration material cannot be subjected to evaluation of the degree of resilience.

In the bone regeneration material according to the present disclosure, the OCP particles are dispersed well in the gelatin which is a polymer material. The well-dispersed state is referred to as "uniformly dispersed state" for convenience of explanation. That is, in the bone regeneration material according to the present disclosure, the OCP particles are hardly aggregated in the gelatin, and the individual OCP particles dispersed in the gelatin are substantially separate from one another. In particular, when the bone regeneration material according to the present disclosure (a bone regeneration material according to Example 1 described below) was observed with a scanning electron microscope (SEM), the gelatin was found to be present in such a manner as to coat (cover) the entire periphery of each OCP particle.

A bone regeneration material according to Comparative Example 2 described below is one prepared using collagen as a polymer material. That is, the bone regeneration material according to Comparative Example 2 is in the form of a composite (OCP/Col) of OCP particles and collagen. Observing this bone regeneration material with a SEM revealed that the collagen was present on some regions of the periphery of the OCP particle but was not present in such a manner as to coat the entire periphery of the OCP particle.

A bone regeneration material according to Comparative Example 1 described below is one prepared using collagen as a polymer material and hydroxyapatite particles (HAp particles) as calcium phosphate compound particles. That is, the bone regeneration material according to Comparative Example 1 is in the form of a composite (HAp/Col) of HAp particles and collagen. When this bone regeneration material was observed with a SEM, the collagen fibers and the HAp particles appeared to be equally dispersed. This observation result leads to the inference that in the HAp/Col of Comparative Example 1 the HAp particles were "kneaded in" the collagen fibers. The HAp/Col in such a state is inferred to easily suffer from falling off of the HAp particles present in the outermost layer of the collagen fiber and therefore from weakening of the collagen framework.

Unlike the conventional bone regeneration materials, the bone regeneration material according to the present disclosure has a structure in which micrometer-sized OCP particles used as calcium phosphate compound particles are coated with gelatin having a predetermined molecular weight. This is a possible reason why the bone regeneration material according to the present disclosure is superior in shape retaining property to the conventional bone regeneration materials. The shape retaining property of the bone regeneration material according to the present disclosure is expected to be further improved by adjusting or varying the various factors described above.

The bone regeneration material disclosed in Patent Literature 3 is also an OCP/Gel. In this bone regeneration material, however, the size of the OCP particles is reduced to the order of nanometers to achieve suitable formability and elastic modulus. Thus, Patent Literature 3 does not impose any limitation on the molecular weight of the gelatin. In the present disclosure, the molecular weight of the gelatin is limited to a particular range, and the size of the OCP particles is controlled in the order of micrometers instead of being reduced to the order of nanometers. This is a possible reason why the bone regeneration material prepared as a composite of the OCP particles and the gelatin was able to exhibit superior shape retaining property.

The bone regeneration material according to the present disclosure can be formed into a desired shape by a known method. The forming method is not limited to any particular method. For example, a mold (such as a metal mold) suitable for the desired shape may be used as described in Patent Literature 3. The shape of the formed bone regeneration material can be adjusted as appropriate to conform to the bone defect site into which the material is implanted.

The bone regeneration material according to the present disclosure can be sterilized by a known method before use. The method for sterilization is not limited to any particular method, and typical examples of the method include radiation sterilization such as gamma sterilization and electron beam sterilization.

The use or application of the bone regeneration material according to the present disclosure is not limited to any particular conditions. Typical examples of living organisms to which the bone regeneration material according to the present disclosure is applicable include mammals such as a mouse, rat, guinea pig, rabbit, dog, cat, monkey, and human. A preferred example is a human.

The bone regeneration material according to the present disclosure has high handleability such as being able to resist breaking down during implantation, and further has high bone regeneration performance. As such, the bone regeneration material according to the present disclosure is not limited to any particular application (purpose), and can be used suitably for various applications (purposes) which require bone regeneration. Specific examples of the applications (purposes) for which the bone regeneration material according to the present disclosure is used include: promoting bone regeneration to repair bone defects such as those caused by therapy for bone tumor or any other disease, those caused by bone fracture or any other external injury, and those caused by extraction of autologous bone; and assisting or replacing autologous bone (allogeneic bone) grafting.

When the bone regeneration material according to the present disclosure is used for any of the above-mentioned applications (purposes), the bone regeneration material may be implanted into the bone defect site or the site of bone grafting to be assisted or replaced. Examples of the site into which the bone regeneration material according to the present disclosure is implanted (namely, the site to which the bone regeneration material is applicable) include bone defect sites present between a bone and a tendon, between a bone and a ligament, and between bones. If the bone regeneration material according to the present disclosure is implanted into a bone defect site or a site of bone grafting to be assisted or replaced in a living organism, absorption of the bone regeneration material component (in particular, the OCP/Gel) and recovery of the bone defect site will be promoted in the living organism.

As described above, the bone regeneration material according to the present disclosure is a bone regeneration material including a composite of a calcium phosphate compound and a polymer material as a main component, and the composite is an OCP-gelatin composite (OCP/Gel) formed by using micrometer-sized octacalcium phosphate particles (OCP particles) as the calcium phosphate compound and using gelatin having a molecular weight in a predetermined range as the polymer material. Thus, when soaked with water and then compressed, the bone regeneration material can remain free of damage such as fracture or breaking down and return substantially to the pre-compression original shape. That is, the bone regeneration material is superior in shape retaining property to conventional bone regeneration materials, and can be obtained as a gelatin-containing bone regeneration material able to resist breaking down during implantation and exhibit high handleability.

EXAMPLES

Hereinafter, the present invention will be described in more detail based on an example and comparative and reference examples. The present invention is not limited to the example described below. Those skilled in the art could make various changes, adaptations, and modifications without departing from the scope of the present invention.
Method for Compression Testing of Bone Regeneration Material A bone regeneration material sample was prepared in the shape of a cube, 10 mm on a side (10 mm×10 mm×10 mm). The bone regeneration material sample was wetted with water and then compressed by means of a compression tester (precision universal testing machine, manufactured by Shimadzu Corporation under the product name "Autograph AG-IS"), and the compression force (test force) and the elastic modulus were measured. In the compression testing, the compression speed of the moving crosshead (crosshead speed) and the compression distance (the length of stroke of the moving crosshead) were set to simulate the following situations: (A) a situation where the bone regeneration material is held with tweezers; and (B) a situation where the bone regeneration material is held between fingers of a user. In this testing, the presence or absence of damage such as fracture or breaking down was examined, and the compression force and elastic modulus were measured.
(A) Simulation of Situation where Bone Regeneration Material is Held with Tweezers The bone regeneration material sample was compressed at a crosshead speed of 10 mm/min and a compression distance of 9 mm, and evaluated for the shape retaining property (the presence or absence of damage such as fracture or breaking down). The change in the compression force [N] acting on the bone regeneration material sample during compression was also measured.
(B) Simulation of Situation where Bone Regeneration Material is Held Between Fingers of User The bone regeneration material sample was compressed at a crosshead speed of 60 mm/min and a compression distance of 7.5 mm, and its elastic modulus [N/mm$^2$] was measured. A test cycle consisting of the compression and the elastic modulus measurement was repeated until the bone regeneration material sample became incompressible or up to 10 times.

For both the situations (A) and (B), the shape retaining property against the compression testing was rated "Good" when the sample did not show damage such as fracture or breaking down after the compression testing. The shape retaining property against the compression testing was rated "Poor" when the sample showed damage such as fracture or breaking down after the compression testing.
Method for Measuring Porosity To measure the pore size and porosity of the bone regeneration material sample, mercury intrusion was performed using a pore size distribution analyzer (manufactured by Micromeritics Instrument Corporation under the product name "AutoPore IV 9500 V1.09"). The measurement conditions were such that the contact angle between the bone regeneration material sample and the mercury was 140° and the surface tension of the mercury was 480 dyne/cm. The pore size and porosity were determined based on the Washburn equation.

Example 1

OCP particles having a particle size of 30 μm were produced by a known method (such as the method described in Patent Literature 3). The OCP particles and gelatin having a molecular weight in the range of 40 to 60 kDa (manufactured by Jellice Co., Ltd. under the product name "RM-50") were used to obtain a formed OCP/Gel composite by the method described in Patent Literature 1. The formed composite was in the shape of a cube, 10 mm on a side (10 mm×10 mm×10 mm). The formed composite was used as the bone regeneration material sample of Example 1.

The physical properties of the bone regeneration material sample of Example 1 were measured and evaluated by simulating the situation (A) where the bone regeneration material is held with tweezers and the situation (B) where the bone regeneration material is held between fingers of a user, as described in "Method for compression testing of bone regeneration material" above. The porosity of the bone regeneration material sample of Example 1 was also measured as described in "Method for measuring porosity" above.

For the simulation of the situation (A), the result of the evaluation of the shape retaining property is shown in Tables 1 and 2, and the change in compression force (test force) with respect to compression distance is shown by a solid line in the graph of FIG. 1. The result of the measurement of the porosity is also shown in Tables 1 and 2. For the simulation of the situation (B), the number of the test cycles and the result of the evaluation of the shape retaining property are shown in Table 1, and the elastic modulus measured in each test cycle is shown by a diamond in the graph of FIG. 2.

Comparative Example 1

The physical property measurement and evaluation were conducted by simulating the situations (A) and (B) in the same manner as in Example 1, except that a commercially-available collagen-containing bone regeneration material sold under the name "ReFit" (registered trademark) was used as the bone regeneration material sample of Comparative Example 1. The bone regeneration material sample of Comparative Example 1 ("ReFit") is in the shape of a cube, 10 mm on a side (10 mm×10 mm×10 mm), just as is the sample of Example 1.

For the simulation of the situation (A), the result of the evaluation of the shape retaining property is shown in Table 1, and the change in compression force (test force) with respect to compression distance is shown by a dotted line in the graph of FIG. 1. For the porosity, the numerical range indicated in the document attached to "ReFit" is shown. For the simulation of the situation (B), the number of the test cycles and the result of the evaluation of the shape retaining property are shown in Table 1, and the elastic modulus measured in each test cycle is shown by a square in the graph of FIG. 2.

Comparative Example 2

A bone regeneration material sample (collagen-containing bone regeneration material) of Comparative Example 2 was obtained in the same manner as the sample of Example 1, except that collagen (manufactured by NH Foods Ltd. under the product name "NMP collagen PS") was used as the polymer material instead of gelatin. The physical properties of the bone regeneration material sample were measured and evaluated by simulating the situations (A) and (B) in the same manner as in Example 1. The porosity measurement was also conducted in the same manner as in Example 1.

For the simulation of the situation (A), the result of the evaluation of the shape retaining property is shown in Table 1 (the change in compression force was not measured). The result of the porosity measurement is also shown in Table 1. For the simulation of the situation (B), the number of the test cycles and the result of the evaluation of the shape retaining property are shown in Table 1, and the elastic modulus measured in the test cycle is shown by a triangle in the graph of FIG. 2.

TABLE 1

| | Polymer material | (A) Shape retaining property | Porosity [%] | (B) Shape retaining property | Number of test cycles |
|---|---|---|---|---|---|
| Example 1 | Gelatin | Good | 92 | Good | 10 |
| Comparative Example 1 | Collagen | Poor | 92-98 | Poor | 3 |
| Comparative Example 2 | Collagen | Poor | 91 | Poor | 1 |

Comparative Example 3

A bone regeneration material sample (gelatin-containing bone regeneration material) of Comparative Example 3 was obtained in the same manner as the sample of Example 1, except that the gelatin used was one having a molecular weight of 8.7 kDa (manufactured by Nippi, Incorporated under the product name "High-grade Gelatin Type AP"). The value of the molecular weight is based on the data presented in the product quality inspection certificate. The physical properties of the bone regeneration material sample were measured and evaluated by simulating the situation (A) in the same manner as in Example 1. The porosity measurement was also conducted in the same manner as in Example 1. The results of the shape retaining property evaluation and porosity measurement are shown in Table 2.

Comparative Example 4

A bone regeneration material sample (gelatin-containing bone regeneration material) of Comparative Example 4 was obtained in the same manner as the sample of Example 1, except that the gelatin used was one having a molecular weight of 80 to 100 kDa (manufactured by Jellice Co., Ltd. under the product name "RM-100"). The physical properties of the bone regeneration material sample were measured and evaluated by simulating the situation (A) in the same manner as in Example 1. The porosity measurement was also conducted in the same manner as in Example 1. The results of the shape retaining property evaluation and porosity measurement are shown in Table 2.

Comparative Example 5

A bone regeneration material sample (gelatin-containing bone regeneration material) of Comparative Example 5 was obtained in the same manner as the sample of Example 1, except that the gelatin used was one having a molecular weight of 230 kDa (manufactured by Nippi, Incorporated under the product name "MediGelatin Type HMG-BP"). The value of the molecular weight is based on the data presented in the product quality inspection certificate. The physical properties of the bone regeneration material sample were measured and evaluated by simulating the situation (A) in the same manner as in Example 1. The porosity measurement was also conducted in the same manner as in Example 1. The results of the shape retaining property evaluation and porosity measurement are shown in Table 2.

TABLE 2

| | Molecular weight of gelatin [kDa] | (A) Shape retaining property | Porosity [%] |
|---|---|---|---|
| Example 1 | 40-60 | Good | 92 |
| Comparative Example 3 | 8.7 | — | — |
| Comparative Example 4 | 80-100 | Poor | 90 |
| Comparative Example 5 | 230 | Poor | 90 |

Comparison of Example with Comparative Examples

Comparing Example 1 with Comparative Examples 1 and 2 based on Table 1 reveals that the gelatin-containing bone regeneration material according to Example 1 successfully exhibited good shape retaining property in both of the simulations of the situation (A) where the bone regeneration material is held with tweezers and the situation (B) where the bone regeneration material is held between fingers of a user. In contrast, the collagen-containing bone regeneration materials according to Comparative Examples 1 and 2, in which the polymer material used was collagen, were fractured or broken down and failed to exhibit sufficient shape retaining property in both of the simulations of the situations (A) and (B).

As seen from FIG. 1, when the gelatin-containing bone regeneration material according to Example 1 was tested by simulating the situation (A), the compression force (test force) increased with increasing compression distance, showed a sharp increase while the compression distance was around 7 to 8 mm, and reached the maximum at the same time as the compression distance reached the maximum (9 mm). The bone regeneration material sample became merely compressed without being fractured and, upon release from the compression, returned substantially to the pre-compression original shape.

For the collagen-containing bone regeneration material according to Comparative Example 1, the compression force (test force) was higher than for the gelatin-containing bone regeneration material according to Example 1 until the compression distance reached about 5 mm; however, the compression force became lower thereafter. Moreover, the collagen-containing bone regeneration material according to Comparative Example 1 was fractured when the compression distance was about 3 mm.

Figure 2:
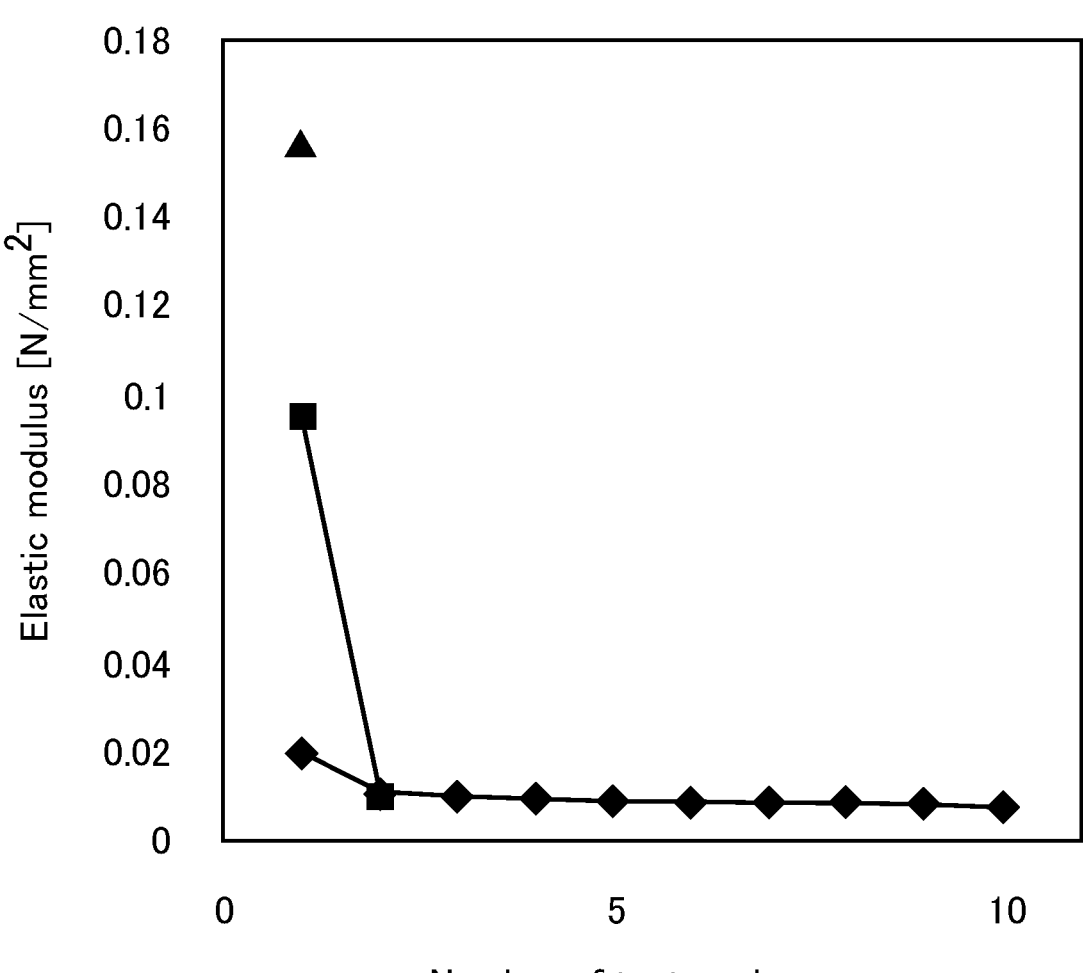
FIG. 2 is a graph showing the elastic modulus measured with respect to the number of test cycles in compression testing of bone regeneration material samples according to Example 1 of the present invention and Comparative Examples 1 and 2.

In the simulation of the situation (B), as seen from Table 1 and FIG. 2, the gelatin-containing bone regeneration material according to Example 1 underwent no substantial change in shape and remained free of damage such as fracture even after the test cycle was repeated 10 times. Additionally, as seen from FIG. 2, the elastic modulus of the gelatin-containing bone regeneration material according to Example 1 was at the maximum in the first compression test cycle and, although showing a decrease in the second compression test cycle, displayed almost no decrease from the second through tenth compression test cycles. Thus, the elastic modulus can be said to have remained substantially unchanged.

In contrast, the collagen-containing bone regeneration material according to Comparative Example 1 lost the original shape in the first compression test cycle, and the measurement of the elastic modulus of this material was impossible in the third test cycle although the measurement was possible until the second test cycle (this is why the number of the test cycles is shown as 3 in Table 1). As seen from FIG. 2, the elastic modulus of the collagen-containing bone regeneration material according to Comparative Example 1 was nearly 0.1 N/mm$^2$ in the first test cycle, but showed a drastic decrease to less than 0.02 N/mm$^2$ in the second test cycle.

The collagen-containing bone regeneration material according to Comparative Example 2 lost the original shape in the first compression test cycle just as did the material according to Comparative Example 1. Additionally, the measurement of the elastic modulus of the material according to Comparative Example 2 was possible only in the first compression test cycle and impossible in the second test cycle. The value of the elastic modulus measured in the first test cycle was higher than that of Comparative Example 1.

Further, comparing Example 1 with Comparative Examples 3 to 5 based on Table 2 reveals that good shape retaining property was successfully achieved in the simulation of the situation (A) when, as in the gelatin-containing bone regeneration material according to Example 1, the molecular weight of the gelatin was in the range as defined in the present disclosure.

The gelatin-containing bone regeneration material according to Comparative Example 3 was not obtained as a bone regeneration material sample with OCP dispersed therein, and was easily broken down upon immersion into water. The gelatin-containing bone regeneration material according to Comparative Example 4 was broken down in the simulation of the situation (A), and the gelatin-containing bone regeneration material according to Comparative Example 5 was fractured in the simulation of the situation (A).

As seen from Table 2, the bone regeneration material samples according to Example 1 and Comparative Examples 1, 2, 4, and 5 (that is, the samples according to all the example and comparative examples other than Comparative Example 3 in which a bone regeneration material sample with OCP dispersed therein was not obtained) had similar levels of porosity.

As described above, the bone regeneration material according to the present disclosure can, when soaked (wetted) with water and then compressed, remain free of damage such as fracture or breaking down and return substantially to the original shape. That is, the bone regeneration material is superior in shape retaining property to conventional bone regeneration materials, and can be obtained as a gelatin-containing bone regeneration material able to resist breaking down during implantation and exhibit high handleability.

Many modifications and other embodiments of the present invention will be apparent to those skilled in the art from the foregoing description. Accordingly, the foregoing description is to be construed as illustrative only, and is provided for the purpose of teaching those skilled in the art the best mode for carrying out the invention. The details of the structure and/or function may be varied substantially without departing from the scope of the invention.

The present invention is not limited to the embodiment described above, and can be modified in various ways without departing from the scope as defined by the appended claims. The technical scope of the present invention encompasses embodiments obtained by combining technical features disclosed in different embodiments or variants.

INDUSTRIAL APPLICABILITY

The present invention can be widely and suitably used in the filed of bone regeneration materials.

The invention claimed is:

1. A bone regeneration material comprising at least a composite of octacalcium phosphate particles and gelatin, the bone regeneration material being a porous body configured to be soaked to a soaked state, the porous body having a plurality of pores, wherein
   a particle size of the octacalcium phosphate particles is 1 μm or more but less than 1 mm,
   an elastic modulus of the bone regeneration material in the soaked state is in a range of 0.01 N/mm$^2$ to 0.0750 N/mm$^2$, and
   a molecular weight or a molecular weight distribution of the gelatin is in a range of 30 kDa to 70 kDa.
2. The bone regeneration material according to claim 1, wherein
   a porosity is in a range of 87% to 98%, the porosity being a volume ratio of the pores present in the porous body, and
   a median size of the pores is in a range of 14 μm to 55 μm.
3. The bone regeneration material according to claim 1, wherein the particle size of the octacalcium phosphate particles is in a range of 1 μm to 200 μm.
4. The bone regeneration material according to claim 1, wherein a mass ratio of the octacalcium phosphate particles to the gelatin in the composite is in a range of 1 to 9.
5. The bone regeneration material according to claim 1, wherein the bone regeneration material maintains a shape retaining property after being subjected to three repeated compressions in each of which the bone regeneration material is compressed to 75% of an original height of the bone regeneration material.
6. The bone regeneration material according to claim 1, wherein the gelatin coats an entire periphery of each of the octacalcium phosphate particles.
7. The bone regeneration material according to claim 6, wherein a porosity is in a range of 87% to 98%, the porosity being a volume ratio of the pores present in the porous body, and a median size of the pores is in a range of 14 μm to 55 μm.

8. The bone regeneration material according to claim 6, wherein the particle size of the octacalcium phosphate particles is in a range of 1 μm to 200 μm.

9. The bone regeneration material according to claim 6, wherein a mass ratio of the octacalcium phosphate particles to the gelatin in the composite is in a range of 1 to 9.

10. The bone regeneration material according to claim 6, wherein the bone regeneration material maintains a shape retaining property after being subjected to three repeated compressions in each of which the bone regeneration material is compressed to 75% of an original height of the bone regeneration material.

* * * * *